United States Patent [19]

Rao

[11] Patent Number: 5,200,534

[45] Date of Patent: Apr. 6, 1993

[54] PROCESS FOR THE PREPARATION OF TAXOL AND 10-DEACETYLTAXOL

[75] Inventor: Koppaka V. Rao, Gainesville, Fla.

[73] Assignee: University of Florida, Gainesville, Fla.

[21] Appl. No.: 851,469

[22] Filed: Mar. 13, 1992

[51] Int. Cl.$^5$ .......................................... C07D 305/14
[52] U.S. Cl. ..................................... 549/510; 549/511
[58] Field of Search ................................. 549/510, 511

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,924,011 | 5/1990 | Denis et al. | 549/510 |
| 4,924,012 | 5/1990 | Colin et al. | 549/510 |

*Primary Examiner*—Alan L. Rotman
*Assistant Examiner*—Ba K. Trinh

[57] ABSTRACT

Taxol, 10-deacetyltaxol and other taxane derivatives are prepared from naturally occurring taxane-7-xylosides by the oxidative-cleavage of the 7-xyloside moieties.

18 Claims, No Drawings

PROCESS FOR THE PREPARATION OF TAXOL AND 10-DEACETYLTAXOL

BACKGROUND OF THE INVENTION

1. Field of the Invention

This invention relates to the preparation of taxol and 10-deacetyltaxol by partial synthesis starting from various naturally occurring taxane-7-xylosides.

2. Related Art

Taxol was first isolated in 1971 from the western yew, Taxus brevifolia by Wani, et al. (*J.Am.Chem.Soc.*, 1971, 93, 2325), who characterized its structure by chemical and X-ray crystallographic methods.

Taxol is a member of the taxane family of diterpenes having the following structure:

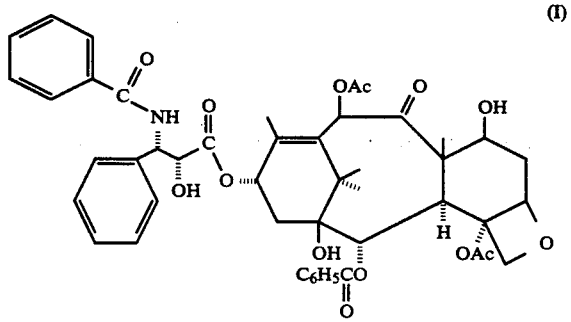

(I)

Taxol and various taxane derivatives, including cephalomannine, are highly cytotoxic and possess strong in vivo activity in a number of leukemic and tumor systems. In recent studies, taxol has become an exceptionally promising cancer chemotherapeutic agent, and is currently in phase II clinical trials in the United States. However, the major problem with the ongoing clinical trial is the limited availability of the compound. Various techniques for increasing the supply of taxol are the subject of active research. Strategies being studied include total synthesis, partial synthesis (from readily available taxol precursors), extraction from Taxus needles, cultivation of Taxus plants, identification of simpler drug analogs, and cell culture production.

Because of the structural complexity of taxol, partial synthesis is a far more viable approach to providing adequate supplies of taxol than total synthesis. The first successful partial synthesis of taxol was developed by J. N. Denis et al., (*J.Am.Chem.Soc.*, 110, 5917 (1988); U.S. Pat. No. 4,924,011). The starting material for the partial synthesis, 10-deacetylbaccatin III, can be extracted in relatively high yield from the leaves of *Taxus blaccata*. However, thus far, no other naturally occurring taxol precursors have been employed in the partial synthesis of taxol.

Senilh, et al. (*J.Nat.Prod.*, 1984, 47, 131) isolated a number of taxane xylosides from the bark of *Taxus baccata*. The major xyloside isolated in that study was 10-deacetyltaxol-7-xyloside (0.022%). 10-deacetyltaxol-7-xyloside was also isolated from the bark of T. brevifolia, together with taxol-7-xyloside and 10-deacetyl-cephalomannine-7-xyloside. Among these various compounds, 10-deacetyltaxol-7-xyloside appears to be one of the major components of the bark. Some batches of bark yield 0.1% or more of this compound which is nearly 5 times as much as that reported earlier by Senilh. Thus, it would be desirable to use 10-deacetyltaxol-7-xyloside as a starting material to synthesize taxol. Unfortunately, all previous attempts at converting 10-deacetyltaxol-7-xyloside have failed. The present invention addresses this need by providing a process for the conversion of 10-deacetyltaxol-7-xyloside and other taxol precursors to taxol.

SUMMARY OF THE INVENTION

Surprisingly, through the step of oxidatively cleaving the xyloside moiety of 10-deacetyltaxol-7-xyloside or taxol-7-xyloside with sodium periodate, these molecules can be converted into 10-deactyltaxol and taxol, respectively. Thus, the present invention provides a process for the preparation of a taxane of the formula:

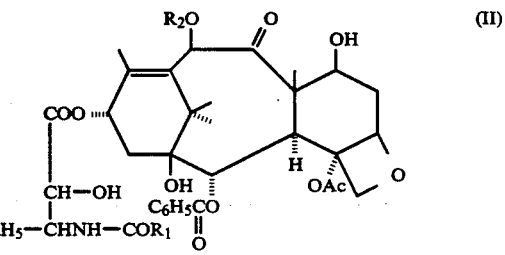

(II)

wherein $R_1$ is $C_6H_5$ or

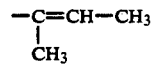

and $R_2$ is hydrogen or acetyl, which comprises the steps of:

(a) reacting a periodate with a taxane-7-xyloside of the formula:

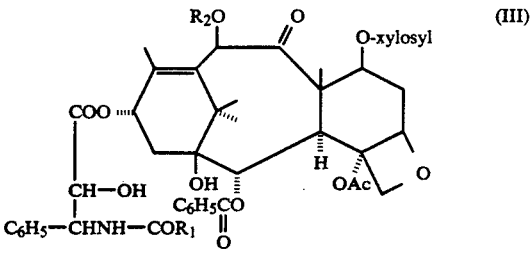

(III)

wherein $R_1$ and $R_2$ are as defined,
in a reaction-inert solvent at a temperature of from about 20° to about 60° C.; and (b) reacting the products obtained in step (a) with phenylhydrazine and acetic acid in a reaction-inert solvent at a temperature of from about 20° to about 60° C.

The present invention further encompasses a process for the preparation of a taxane of the formula:

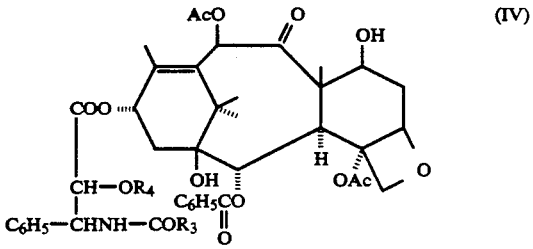

(IV)

wherein $R_3$ is $C_6H_5$ or

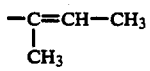

and $R_4$ is hydrogen or acetyl, which comprises the steps of:

(a) reacting a periodate with a taxane-7-xyloside of the formula:

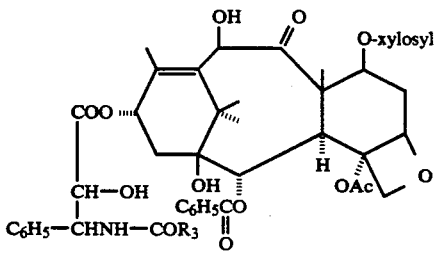

wherein $R_3$ is as defined
in a reaction-inert solvent at a temperature from about 20° to about 60° C.;

(b) reacting the products obtained in step (a) with an acetylating agent in a reaction-inert solvent at a temperature from about 0° to about 100° C.; and (c) reacting the acetylated products obtained in step (b) with phenylhydrazine and acetic acid in a reaction-inert solvent at a temperature of from about 20° to about 60° C.

The present invention also encompasses a process for the preparation of a taxane of the formula (VI):

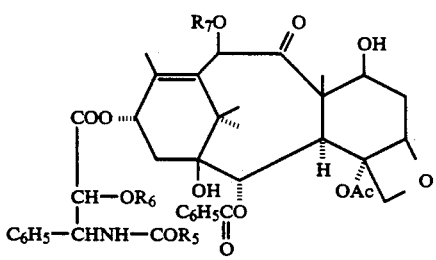

wherein $R_5$ is $C_6H_5$ or

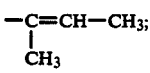

$R_6$ is hydrogen or an acyl selected from the group consisting of benzoyl, butyryl, carbobenzoxyalanyl, propionyl, succinyl, and trifluoroacetyl, and $R_7$ is an acyl selected from the group consisting of benzoyl, butyryl, carbobenzoxyalanyl, propionyl, succinyl, and trifluoroacetyl,
with the proviso that when $R_6$ is an acyl, $R_6$ and $R_7$ are the same, which comprises the steps of:

(a) reacting a periodate with a taxane-7-xyloside of the formula:

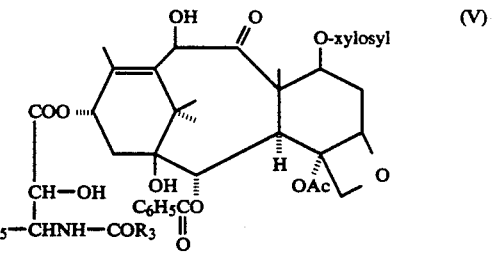

wherein $R_3$ is $C_6H_5$ or

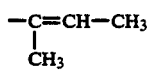

in a reaction-inert solvent at a temperature of from about 0° to about 60° C.;

(b) reacting the products obtained in step (a) with an acylating agent in a reaction-inert solvent; and (c) reacting the acylated products obtained in step (b) with phenylhydrazine and acetic acid in a reaction-inert solvent at a temperature of from about 20° to 60° C.

The present invention still further encompasses a process for the preparation of taxol or cephalomannine, comprising the step of deacetylating 2'-acetyl group of a compound of formula (IV) wherein $R_4$ is acetyl.

The present invention includes a process for the preparation of 10-acyl-10-deacetyltaxol or 10-acyl-10-deacetylcephalomannine, comprising the step of deacylating 2'-acyl group of a compound of formula (VI) wherein $R_6$ is acyl.

The present invention further includes a process of converting 10-deacetyltaxol and 10-deacetylcephalomannine into taxol and cephalomannine, respectively.

DETAILED DESCRIPTION OF THE INVENTION

The present invention is based in part on the discovery that the xyloside moiety of a taxane-7-xyloside can be oxidatively cleaved by the use of sodium periodate or other periodates followed by treatment with phenylhydrazine to give 7-hydroxyl-taxane (taxol) derivatives. The oxidative cleavage reaction sequence employed in the present invention would also be applicable to taxane glycosides other than xylosides.

Hydrolysis of a taxane xyloside by conventional methods such as acidic treatment on heating is not suitable because the taxane skeleton is susceptible to such treatment. Attempted enzymatic cleavage of the xyloside was also unsuccessful, as reported by Senilh, et al., op cit.

According to one aspect of the present invention, a taxane-7-xyloside of the formula (III) can be converted to a taxane of the formula (II).

In the present oxidative-cleavage process, the oxidation of the xyloside is carried out by reaction of the taxane (III) with at least one-molar equivalent of periodate in a reaction-inert solvent, preferably a water-miscible solvent.

Suitable periodates for use in the invention are paraperiodic acid, $H_5IO_6$, potassium metaperiodate, sodium metaperiodate, and $NaIO_4$.

As employed herein, the term "reaction-inert solvent" refers to a solvent which does not significantly interact with reactants, reagents, intermediates or product in a manner which significantly reduces the yield of the desired products.

Examples of suitable reaction-inert solvents include methanol, ethanol, t-butyl alcohol, dioxane and acetic acid. Water can be used as a cosolvent. Also, other organic solvents can be used to dissolve water-insoluble compounds.

The cleavage of 1,2-diols by periodate is usually most rapid in the acidity range of pH 1-6. An acidic solvent system such as acetic acid or the presence of an acid is, therefore, preferred. However, alternatively, neutral conditions such as in the presence of excess sodium bicarbonate as a buffer can also be employed. Reaction temperature is not critical, but is preferably in the range of 20° to 60° C. Under these conditions, reaction is complete in from about 30 minutes to four hours, providing a dialdehyde product resulting from the cleaved 1,2-diols.

The second step of the present oxidative-cleavage process involves degradation of the dialdehyde product with phenylhydrazine and acetic acid. This step is carried out by reacting the dialdehyde product, without further purification, with at least two molar equivalents of phenylhydrazine in the presence of acetic acid in a reaction-inert solvent.

Examples of suitable reaction-inert solvents include methanol, ethanol, t-butyl alcohol, and dioxane. Again, temperature is not critical, but is preferably in the range of 20°-60° C. Under these conditions, the desired products of formula (II) are readily formed in about one hour.

The products of formula (II) are isolated and purified by standard methods well known to those skilled in the art, such as recrystallization or column chromatography.

The compound of formula (III) wherein $R_1$ is $C_6H_5$ and $R_2$ is hydrogen (10-deacetyl-taxol-7-xyloside) is converted through the above two-step process, to a product of formula (II) wherein $R_1$ is $C_6H_5$ and $R_2$ is hydrogen (10-deacetyl-taxol).

Similarly, the compound of formula (III) wherein $R_1$ is $C_6H_5$ and $R_2$ is acetyl (taxol-7-xyloside) can be converted to a product of formula (II) wherein $R_1$ is $C_6H_5$ and $R_2$ is acetyl (taxol).

Further, the compound of formula (III) wherein $R_1$ is

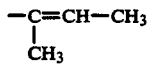

and $R_2$ is hydrogen (10-deacetylcephalomannine-7-xyloside) can be converted to a product of formula (II) wherein $R_1$ is

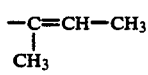

and $R_2$ is hydrogen (10-deacetylcephalomannine).

Still further, the compound of formula (III) wherein $R_1$ is

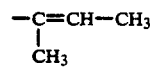

and $R_2$ is acetyl (cephalomannine-7-xyloside) can be converted to a product of formula (II) wherein $R_1$ is

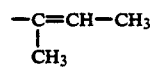

and $R_2$ is acetyl (cephalomannine).

In another aspect of this invention, both 10-deacetyltaxol and 10-deacetylcephalomannine are then acetylated at the 10-position by a method involving the selective protection of the 7- and 2'-hydroxyl groups, acetylation and deprotection, producing the desired taxol and cephalomannine, respectively.

Acetylation can be carried out by reacting the products with a suitable acetylating agent such as excess acetyl chloride or acetyl anhydride. The acylation reaction is usually conducted in a reaction-inert solvent. Preferably, acetylation is conducted in the presence of a tertiary amine, at a temperature in the range from 0° to 100° C. Reaction-inert solvents which can be used in this acylation are: chlorinated hydrocarbons, such as chloroform and dichloromethane; ethers, such as diethyl ether and tetrahedrofuran; low molecular weight esters, such as ethyl acetate and butyl acetate; low molecular weight aliphatic ketones, such as acetone and methyl ethyl ketone; tertiary amides, such as N,N-dimethyl formamide and N-methylpyrridone; acetonitrile; and mixtures thereof. The typical tertiary amines which can be used are triethylamine, tributylamine, diisopropylethylamine, pyridine and 4-dimethylaminopyridine.

Prior to the acetylation step, the 10-deacetyltaxanes are treated with a suitable protecting agent to protect its 7- and 2'-hydroxyl position. Suitable protecting groups include chloroacetate, trichloroacetate, trichloroethyl carbonate, and triethylsilyl ether. A preferred protection method involves the use of chloroacetic anhydride in a reaction inert solvent, preferably in the presence of a tertiary amine. The reaction-inert solvents and the tertiary amines usable in this step are not significantly different from those described earlier for the acetylation step.

Once acetylation has been completed, the deprotection of the 7- and 2'-hydroxyl protecting groups is carried out by treating with a suitable deprotecting agent. When the protecting group is chloroacetate, the deprotection procedure employs thiourea. Other deprotecting agents that can be used include aminoethanethiol, ethylene diamine and o-phenylene diamine.

Following the protection, acetylation, and deprotection steps, taxol and cephalomannine can be derived from 10-deacetyltaxol and 10-deacetylcephalomannine, respectively.

According to a further aspect of the present invention, the compounds of formula (V) are first subjected to the oxidative cleavage step and the reaction products are acetylated without further purification. This acetylation is carried out in the same manner as that described for the acetylation of 10-deacetyltaxol and 10-deacetyl cephalomannine.

The acetylation products are then exposed to the conditions employed for the second step of the present oxidative-cleavage process, namely treatment with phenylhydrazine and acetic acid. Prolonged treatment tends to cause the hydrolysis of the initially-formed 2'-acetyl group. Products thus formed are compounds of formula (IV) wherein $R_4$ can be hydrogen or acetyl.

When the starting material is 10-deacetyltaxol-7-xyloside, the resulting products can be 2'-acetyltaxol and taxol. Each product can readily be purified, e.g., by recrystallization or column chromatography.

The compound of formula (IV) wherein $R_4$ is acetyl may be selectively hydrolyzed at the 2'-acetyl position, thus providing a compound of formula (IV) wherein $R_4$ is hydrogen. The hydrolysis can be carried out in the presence of a weak base in a reaction-inert solvent, e.g., lower alcohol. Suitable base agents include sodium bicarbonate, potassium bicarbonate, dimethylamine, and diethylamine. A particularly preferred solvent is methanol. Reaction is normally conducted at ambient temperature.

More conveniently, the mixture of the acetylated products, without separation and purification, are exposed to the afore-described selective hydrolysis conditions, thus yielding only the compound of formula (IV) wherein $R_4$ is hydrogen.

In a similar manner to the conversion of compounds (V) to compounds (IV), the compounds (V) are first subjected to the oxidative cleavage step and the reaction product are acylated without purification. Suitable acylating agents which can be used include succinic anhydride, propionic anhydride, butyric anhydride, benzoyl chloride, carbobenzoxy alanyl chloride, and trifluoroacetic anhydride. This acylation is carried out under substantially the same conditions as those described for the above-indicated acetylations.

The acylation products are then exposed to the conditions employed for the second step of the present oxidative-cleavage process. Products thus formed are compounds of formula (VI).

When the stating material is 10-deacetyltaxol-7-xyloside, the resulting product can be 2', 10-diacyl 10-deacetyl taxol and 10-acyl-10-deacetyl-taxol. The diacyl-taxol may be hydrolyzed with a base in substantially the same manner as that used for the selective deacetylation of the compounds (IV), providing 10-acyl-10-deacetyl-taxol.

The taxane 7-xylosides of formula (III) and (V), required as starting materials for the invention, are available by the isolation from the taxus species according to the methods well known in the art (see, for example, the references to 10-deacetyltaxol-7-xyloside cited above).

The process of this invention allows the preparation of taxol in a highly efficient manner from various taxane-7-xylosides which have not been hitherto utilized.

The present invention is illustrated by the following examples. However, it should be understood that the invention is not limited to the specific details of these examples.

EXAMPLE 1

10-Deacetyltaxol

To a solution of 0.5 g of 10-deacetyltaxol-7-xyloside in 25 ml of methanol/chloroform (4:1) was added 0.3 g of sodium periodate and 2 ml of 1N sulfuric acid. Stirring was continued for about 3 hours at room temperature. The reaction mixture was diluted with 100 ml of water and the organic phase was extracted with 50 ml of chloroform ($\times 3$). The organic extracts were concentrated to dryness, yielding 0.5 g of a product. The product (0.5 g) was dissolved in 10 ml of methanol and 5 ml of 50% aqueous acetic acid. The resulting solution was mixed with 0.2 ml of phenylhydrazine. The mixture was heated at 50°–60° C. for 1 hour. After cooling, the reaction mixture was diluted with 20 ml of water and the organic phase was extracted with 20 ml of chloroform ($\times 2$). The combined chloroform extract was concentrated to dryness under reduced pressure. The resulting residue was chromatographed on 10 g of silica gel using chloroform/ligroin (2:1) as eluant. The eluant was changed to chloroform, 2–5% acetone in chloroform, and finally, 2–5% methanol in chloroform.

The appropriate fractions were combined and concentrated under reduced pressure. The residue was recrystallized from chloroform to give 0.2 g of the title compound, m.p. 192°–196°.

The spectroscopic characteristics of the product are identical in all respects with an authentic sample (as reported in J. L. McLaughlin, et al., *J. Nat. Prod.*, 1981, 44, 312).

EXAMPLE 2

10-deacetylcephalomannine

In the manner of the procedure of EXAMPLE 1, 0.5 g of 10-deacetylcephalomannine-7-xyloside was oxidatively cleaved to give 0.2 g of the title compound, identical in all respects with an authentic sample (R. W. Miller, et al., *J. Org. Chem.*, 1981, 46).

EXAMPLE 3

Taxol

In the manner of the procedure of EXAMPLE 1, 0.5 g of taxol-7-xyloside was oxidatively cleaved. The product, after treatment with phenylhydrazine, was taken up in 25% acetonitrile in water and applied to a column of 10 g of C-18 reverse phase silica. The column was eluted with a gradient of acetonitrile in water (30, 35, 40, 45 and 50%).

The appropriate fractions were combined and concentrated under reduced pressure. The residue was recrystallized from acetonitrile/water to give 0.2 g of the title compound, identical in all respects with an authentic sample (Wani, et al., op. cit.).

EXAMPLE 4

Cephalomannine

In the manner of the procedure of EXAMPLE 1 as modified in Example 3, 0.5 g of cephalomannine-7-xyloside was oxidatively cleaved to give 0.2 g of the title compound, identical in all respects with an authentic sample (R. W. Miller, op. cit.).

EXAMPLE 5

Taxol

To a solution of 1 g of 10-deacetyltaxol-7-xyloside in 50 ml of methanol/chloroform (4:1) was added 0.6 g of sodium periodate and 4 ml of 1N sulfuric acid. Stirring was continued for about 3 hours at room temperature. The reaction mixture was diluted with 50 ml of water and the organic phase was extracted with 50 ml of chloroform ($\times 2$). The organic extracts were concentrated to dryness, yielding a colorless solid (1.0 g).

The solid (1.0 g) was dissolved in 5 ml of acetic anhydride and 1 ml of pyridine. The solution was heated at 100° C. for about 30 minutes. After cooling, the mixture was diluted with 50 ml of water and 1 g of a colorless solid was collected by filtration. The resulting solid (1 g) was dissolved in 20 ml of methanol/chloroform (4:1). To the solution was added 3 ml of acetic acid and 0.5 ml of phenylhydrazine. The mixture was heated at 50°-60° C. for about 3 hours. After cooling, the reaction mixture was diluted with 20 ml of water and the organic phase was extracted with 20 ml of chloroform (×2). The combined chloroform extract was concentrated to dryness under reduced pressure. The resulting residue was chromatographed on a reverse phase C-8 column using 25% acetonitrile in water as eluant. A gradient of acetonitrile in water (30, 35, 40, 45 and 50% acetonitrile) was successively used as eluant. The appropriate fractions were combined and concentrated under reduced pressure. The earlier fractions gave 0.1 g of the title compound. The later fractions gave 0.5 g of 2'-acetyltaxol, which was recrystallized rom acetone/ligroin to afford 0.4 g of a colorless crystalline solid. The product thus obtained was identical in all respects with an authentic sample (W. Mellado, et al., Biochem. Biophys. Res. Commun., 1984, 124, 329).

EXAMPLE 6

10-Succinyl-10-deacetyltaxol

In the manner of the procedure of Example 1, 0.5 g of 10-deacetyltaxol-7-xyloside was oxidatively cleaved. The oxidation product was extracted with chloroform, concentrated, and dissolved in 2 ml of pyridine. To the pyridine solution was added 1 g of succinic anhydride. The mixture was heated at 100° C. for 1 hour. After the reaction was complete (monitored by tlc), the cooled mixture was diluted with water. Upon standing for 30 minutes, the mixture was acidified and extracted with chloroform (×2). The chloroform extracts were washed with aqueous sodium bicarbonate solution, and concentrated to dryness under reduced pressure.

The resulting product was dissolved in 20 ml of methanol. To the solution was added 3 ml of acetic acid and 0.3 ml of phenylhydrazine. The mixture was heated at 70°-90° C. for about 2 hours. When the reaction was complete, the reaction mixture was diluted with 30 ml of water and the organic phase was extracted with chloroform (×2). The combined chloroform extract was concentrated to dryness under reduced pressure. The residual solid was chromatographed on a silica gel column using 2:1 chloroform/ligroin as eluant. The eluant was successively changed to chloroform, 2-5% acetone in chloroform, and 2-5% methanol in chloroform. The product recovered was 2', 10-disuccinyl-10-deacetyltaxol. The disuccinate (0.2 g) was dissolved in 10 ml of methanol and treated with an equal volume of dimethylamine in methanol (about 0.2-0.8%). The reaction was monitored by tlc or HPLC until hydrolysis was complete. The reaction mixture was acidified by addition of a few drps of acetic acid and concentrated to dryness under reduced pressure. The resulting solid was recrystallized from acetone/ligroin to yield 0.1 g of the title compound.

PREPARATION 1

Taxol from 10-Deacetyltaxol

To a solution of 0.5 g of 10-deacetyltaxol in 2 ml pyridine was added 0.5 g of chloroacetic anhydride at room temperature for 1 hour. The reaction mixture was diluted with water and the resulting solid was filtered. This solid was chromatographed on 10 g of silica gel using chloroform/acetone (2-5%) as eluant. The appropriate fractions were combined and concentrated under reduced pressure to give a solid, which was recrystallized from acetone/hexane. The resulting product (0.5 g) was heated in a mixture of 2 ml of acetic anhydride and 1 ml of pyridine at 100° C. for 30 minutes.

To a solution of 0.2 g of the product in 10 ml of ethanol was added 0.2 g of thiourea and 0.1 g of sodium bicarbonate. The resulting mixture was stirred at room temperature for 1 hour, and diluted with water. The solid precipitated was collected by filtration and then recrystallized from acetone/ligroin to give 0.3 g of taxol, identical in all respects with an authentic sample.

PREPARATION 2

Taxol from 2'-acetyltaxol

A solution 0.2 g of 2'-acetyltaxol in 10 ml of methanol was treated with aqueous dimethylamine to make a 0.2% solution of dimethylamine. The reaction mixture was monitored by tlc until the hydrolysis was nearly complete. The reaction mixture was then concentrated to dryness under reduced pressure and the solid crystallized from acetone/ligroin to yield 0.12 g of a colorless crystalline solid, identical in all respects with taxol The invention now being fully described, it will be apparent to one of ordinary skill in the art that many changes and modifications can be made without departing from the spirit or scope of the invention.

I claim:

1. A process for the preparation of a taxane of the formula

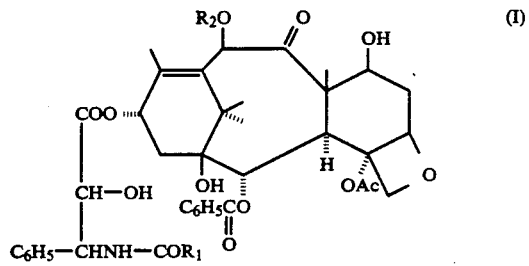

wherein $R_1$ is $C_6H_5$ or

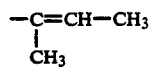

and $R_2$ is hydrogen or acetyl, which comprises the steps of:

(a) reacting a periodate with a taxane-7-xyloside of the formula:

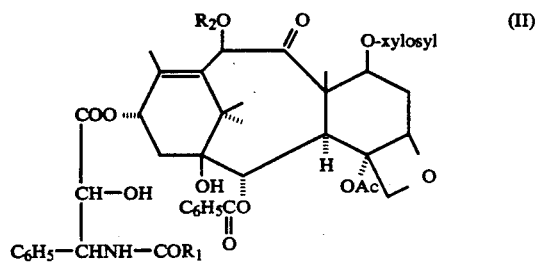

wherein R₁ and R₂ are as defined in a reaction-inert solvent at a temperature of from about 0° to about 60° C.; and (b) reacting the products obtained in step (a) with phenylhydrazine and acetic acid in a reaction-inert solvent at a temperature of from about 20° to about 60° C.

2. The process according to claim 1, wherein the periodate used in step (a) is sodium periodate.

3. The process according to claim 1, wherein step (a) is carried out at room temperature.

4. The process according to claim 1, further comprising the step of acetylating the compound of formula (I) wherein R₂ is hydrogen to produce the compound of formula (I) wherein R is acetyl.

5. The process according to claim 4, wherein prior to the step of acetylation the 7- and 2'-hydroxyls of the compound is protected and after the acetylation the 7- and the 2'-hydroxyl is deprotected.

6. The process according to claim 5, wherein the acetylation is carried out by contacting the compound with acetic anhydride in the presence of pyridine at a temperature of about 0° to 100° C.

7. A process for the preparation of a taxane of the formula

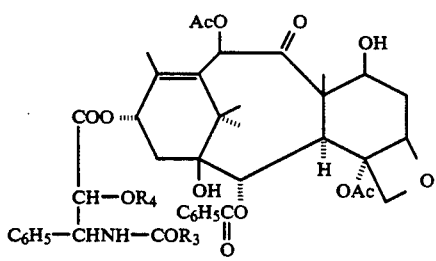

wherein R₃ is C₆H₅ or

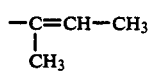

and R₄ is hydrogen or acetyl, which comprises the steps of:

(a) reacting a periodate with a taxane-7-xyloside of the formula:

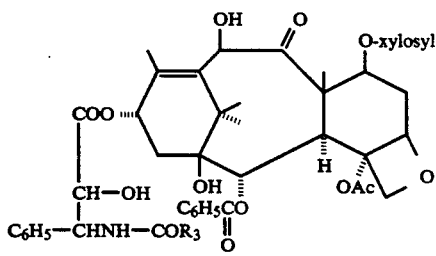

wherein R₃ is as defined in a reaction-inert solvent at a temperature from about 0° to about 60° C.;

(b) reacting the products obtained in step (a) with an acetylating, agent in a reaction-inert solvent; and (c) reacting the acetylated products obtained in step (b) with phenylhydrazine and acetic acid in a reaction-inert solvent at a temperature of from about 20° to about 60° C.

8. The process according to claim 7, wherein the periodate used in step (a) is sodium periodate.

9. The process according to claim 7, wherein step (a) is carried out at room temperature.

10. The process according to claim 7, wherein the acetylating agent is acetic anhydride.

11. The process according to claim 10, wherein the reaction-inert solvent used in step (b) is pyridine.

12. The process according to claim 7, wherein step (b) is carried out at about 0° to 100° C.

13. The process according to claim 7, further comprising the step of deacetylating the compound of formula (III) wherein R₄ is acetyl to produce the compound of formula (III) wherein R₄ is hydrogen.

14. The process according to claim 13, wherein the deacetylation is carried out by contracting the compound of formula (III) wherein R₄ is acetyl with dimethylamine in methanol.

15. A process for the preparation of a taxane of the formula:

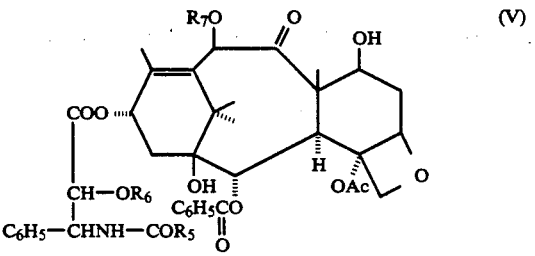

wherein R₅ is C₆H₅ ir

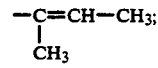

R₆ is an acyl selected from the group consisting of benzoyl, butyryl, carbobenzoxyalanyl, propionyl, succinyl, and trifluoroacetyl or hydrogen; and R₇ is an acyl selected from the group consisting of benzoyl, butyryl, carbobenzoxyalanyl, propionyl, succinyl, and trifluoroacetyl, with the proviso that when R₆ is an acyl, R₆ and R₇ are the same, which comprises the steps of:

(a) reacting a periodate with a taxane-7-xyloside of the formula:

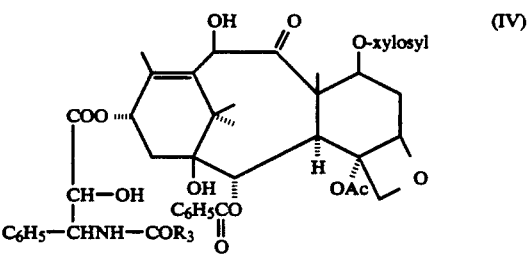

wherein R₃ is C₆H₅ or

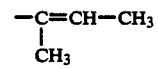

in a reaction-inert solvent at a temperature of from about 0° to about 60° C.;

(b) reacting the products obtained in step (a) with an acylating agent in a reaction-inert solvent; and
(c) reacting the acylated products obtained in step (b) with phenylhydrazine and acetic acid in a reaction-inert solvent at a temperature of from about 20° to 60° C.

16. The process according to claim 15, further comprising the step of deacylating the compound of formula (V) wherein $R_6$ is acyl to produce the compound of formula (V) wherein $R_6$ is hydrogen.

17. The process according to claim 16, wherein the deacylation is carried out by contracting the compound of formula (V) wherein $R_6$ is acyl with dimethylamine in methanol.

18. The process according to claim 15 wherein $R_7$ is succinyl.

* * * * *

UNITED STATES PATENT AND TRADEMARK OFFICE
CERTIFICATE OF CORRECTION

PATENT NO. : 5,200,534

DATED : April 6, 1993

INVENTOR(S) : Koppaka V. Rao

It is certified that error appears in the above-identified patent and that said Letters Patent is hereby corrected as shown below:

Column 1: line 12: "Taxus brevifolia" should read --*Taxus brevifolia*--; lines 33-34: "in vivo" should read --*in vivo*--; lines 61-62: "T. brevifolia" should read --*T. brevifolia*--.

Column 4: line 66: "NalO$_4$" should read --NaIO$_4$--.

Column 9: line 19: "rom" should read --from--.

Column 12: line 34: "ir" should read --or--.

Signed and Sealed this

Fourth Day of January, 1994

BRUCE LEHMAN

*Attest:*

*Attesting Officer*  Commissioner of Patents and Trademarks